United States Patent [19]

Khazai et al.

[11] Patent Number: 5,258,347
[45] Date of Patent: * Nov. 2, 1993

[54] PROCESS OF OXIDIZING ALIPHATIC HYDROCARBONS EMPLOYING A MOLYBDATE CATALYST COMPOSITION

[75] Inventors: Bijan Khazai; Craig B. Murchison; G. Edwin Vrieland, all of Midland, Mich.

[73] Assignee: The Dow Chemical Company, Midland, Mich.

[*] Notice: The portion of the term of this patent subsequent to Nov. 27, 2007 has been disclaimed.

[21] Appl. No.: 890,972

[22] Filed: May 29, 1992

Related U.S. Application Data

[60] Division of Ser. No. 505,751, Apr. 6, 1990, Pat. No. 5,146,031, which is a continuation-in-part of Ser. No. 383,107, Jul. 20, 1989, Pat. No. 4,973,791.

[51] Int. Cl.$^5$ .............................................. B01J 23/00
[52] U.S. Cl. ................................... 502/306; 502/524; 585/624; 585/630; 585/631; 585/658; 585/663
[58] Field of Search ................ 585/624, 630, 631, 658, 585/663; 502/306, 524

[56] References Cited

U.S. PATENT DOCUMENTS

| | | |
|---|---|---|
| 3,119,111 | 1/1964 | McDonald et al. |
| 3,180,903 | 4/1965 | Lindquist et al. |
| 3,488,402 | 1/1970 | Michaels et al. |
| 3,759,844 | 9/1973 | Yamaguchi et al. |
| 3,769,238 | 10/1973 | Tauster et al. |
| 3,862,256 | 1/1975 | Isailingold et al. |
| 3,867,305 | 2/1975 | Flanigen et al. |
| 3,895,051 | 7/1975 | Umemura et al. |
| 4,144,197 | 3/1979 | Riesser. |
| 4,152,300 | 5/1979 | Riesser. |
| 4,170,570 | 10/1979 | Zagata et al. |
| 4,172,854 | 10/1979 | Ellis et al. ........................ 585/445 |
| 4,220,560 | 9/1980 | Anquetil et al. |
| 4,229,604 | 10/1980 | Tmenov et al. |
| 4,250,346 | 2/1981 | Young et al. ..................... 585/658 |
| 4,309,361 | 1/1982 | Suresh et al. |
| 4,336,409 | 6/1982 | Yamamoto et al. ............... 585/622 |
| 4,388,223 | 6/1983 | Ferlazzo et al. |
| 4,430,517 | 2/1984 | Imai et al. ........................ 585/660 |
| 4,447,558 | 5/1984 | Sasaki et al. ..................... 502/215 |
| 4,451,683 | 5/1984 | Davies et al. |
| 4,471,070 | 9/1984 | Siefert et al. .................... 502/302 |
| 4,506,032 | 3/1985 | Imai et al. ....................... 502/223 |
| 4,547,615 | 10/1985 | Yamamoto ....................... 585/621 |
| 4,559,320 | 12/1985 | Reusser ........................... 502/251 |
| 4,596,787 | 6/1986 | Manyik et al. ................... 502/312 |
| 4,711,930 | 12/1987 | Hoelderich et al. .............. 502/209 |
| 4,728,635 | 3/1988 | Bhattacharyya et al. ......... 502/304 |
| 4,746,753 | 5/1988 | Brazdil et al. ................... 558/324 |
| 4,797,381 | 1/1989 | Bartek et al. .................... 502/202 |
| 4,912,078 | 3/1990 | Krijgsman ....................... 502/524 |
| 4,973,791 | 11/1990 | Vrieland .......................... 585/624 |

OTHER PUBLICATIONS

Derwent 06949C/04 (1980).
Derwent 75459 E/36 (1982).
Chemical Abstracts 104:131946b (1986).
Derwent 86-316078/48.
Derwent 85-232465/38.

*Primary Examiner*—Patrick P. Garvin
*Assistant Examiner*—E. D. Irzinski
*Attorney, Agent, or Firm*—Marie F. Zuckerman

[57] ABSTRACT

A process for the production of olefins and diolefins, such as 1,3-butadiene, comprising contacting an aliphatic hydrocarbon, such as butane, with a heterogeneous catalyst composition containing reactive oxygen under reaction conditions such that a more highly unsaturated aliphatic hydrocarbon is selectively formed in a high productivity. The catalyst is a composition comprising (a) a support component of magnesia and alumina and/or magnesium aluminate spinel, and (b) a catalyst component of magnesia, an oxide of molybdenum, a Group IA metal oxide promoter, and optionally vanadium oxide. Catalysts of high surface area and high attrition resistance are claimed.

21 Claims, No Drawings

PROCESS OF OXIDIZING ALIPHATIC HYDROCARBONS EMPLOYING A MOLYBDATE CATALYST COMPOSITION

CROSS-REFERENCE TO RELATED APPLICATION

This is a divisional of application Ser. No. 505,751 filed Apr. 6, 1990, now U.S. Pat. No. 5,146,031 which is a continuation-in-part of application Ser. No. 383,107, filed Jul. 20, 1989 now U.S. Pat. No. 4,973,791.

BACKGROUND OF THE INVENTION

This invention pertains to the oxidation of aliphatic hydrocarbons, such as alkanes and monoolefins, in the presence of a molybdate catalyst to form more highly unsaturated aliphatic hydrocarbons.

Unsaturated aliphatic hydrocarbons, such as monoolefins and diolefins, are useful as monomers and comonomers in the preparation of polyolefin plastics.

U.S. Pat. No. 3,119,111 discloses a process for the oxidative dehydrogenation of a $C_4$ to $C_6$ alkane having a four carbon chain to a 1,3-alkadiene. The reaction occurs in the presence of oxygen and a catalyst containing an alkali metal molybdate, such as lithium molybdate. It is taught that the catalyst can be employed with a carrier material, such as powdered alumina. Disadvantageously, this process requires potentially explosive mixtures of alkanes and oxygen. More disadvantageously, the catalyst of this process contains a high concentration of alkali metal which lowers catalytic activity.

U.S. Pat. No. 3,180,903 discloses a process for the dehydrogenation of aliphatic hydrocarbons containing from two to five carbon atoms. Butanes, for example, can be converted to butenes and butadienes. The catalyst is taught to contain chromium oxides or molybdenum oxides supported on a gel-type alumina. Optionally, the catalyst may contain one or more alkali metal oxides. Disadvantageously, this process is limited to a low hydrocarbon conversion and a low ultimate yield of butadiene.

U.S. Pat. No. 3,488,402 teaches the dehydrogenation of butane to butene and butadiene in the presence of two catalysts. The first is a dehydrogenation catalyst containing alumina, magnesia, or combinations thereof, promoted with an oxide of a metal of Groups IVB, VB or VIB, such as chromia, vanadium oxide or molybdenum oxide. The second catalyst is an oxidation catalyst comprising a Group IVA or VA vanadate, molybdate, phosphomolybdate, tungstate or phosphotungstate. Disadvantageously, this process comprises two steps and requires subatmospheric pressures. Even more disadvantageously, this process produces low butadiene selectivity and yield.

U.S. Pat. No. 3,862,256 discloses a process for the oxidative dehydrogenation of paraffin hydrocarbons, such as butane, over a catalyst containing oxy compounds of molybdenum and magnesium, and optionally, vanadium and/or silicon. When butane is contacted with the catalyst, the products include butenes and butadiene; however, the selectivity and space-time yield of butadiene are lower than desired. In addition, the feed contains hydrocarbon and oxygen, which is not desirable for safety reasons. Finally, the magnesium oxide support does not possess the toughness and attrition resistance needed for fluid bed or transport reactors.

U.S. Pat. No. 4,229,604 discloses a process for the oxidative dehydrogenation of a paraffin, such as butane, to unsaturated hydrocarbons, such as butenes and butadiene. The catalyst is an oxide of molybdenum deposited on a carrier. The carrier is selected from the group consisting of granulated porous crystalline silica modified with magnesia, magnesium-titanium oxides, and magnesium-aluminum oxides. It is taught that during the carrier preparation silicates of the alkali metals or titanates or aluminates of magnesium are formed. It is further taught that on the surface of the catalyst there exists an active magnesium molybdate. Disadvantageously, the catalyst produces a selectivity and space-time yield of butadiene which are too low for industrial use. The low activity of this catalyst is attributed in part to its low surface area.

U.S. Pat. No. 4,388,223 discloses the oxidizing dehydrogenation of butene-1 to butadiene. The catalyst comprises (a) a crystalline phase (I) consisting of one or more molybdates belonging to the monoclinic system, chosen from ferric, aluminum, cerium, and chromium molybdates, (b) a crystalline phase (II) consisting of one or more molybdates belonging to the monoclinic system, including magnesium molybdate, and (c) one or more promoter elements including vanadium. It is also taught that the catalyst may comprise alkaline elements such as potassium, lithium, cesium and magnesium and/or acidic elements, such as phosphorus and silicon. This process co-feeds hydrocarbon and oxygen, which is undesirable for safety reasons. Moreover, the catalyst does not have the toughness and attrition resistance required for fluid bed or transport reactors.

U.S. Pat. No. 3,769,238 teaches a catalyst composition comprising (a) a catalytically-active material containing a divalent metal, such as magnesium, tetravalent molybdenum, and oxygen in chemically combined form, and (b) a support comprising deacidified alumina. The support is deacidified with a small amount of a Group IA metal oxide, such as cesium oxide. The composition of the catalyst, stated in gram-atoms of metal per 100 moles of alumina, is as follows: divalent metal, 1 to 60 gram-atoms; molybdenum, 1.5 to 90 gram-atoms; Group IA metal, 1 to 5 gram-atoms.

While the oxidation of aliphatic hydrocarbons is well researched in the prior art, the selectivity and space-time yield to particular unsaturated hydrocarbons, such as diolefins, fall short of those which are desired for commercial exploitation. Moreover, the catalysts employed in the prior art do not possess the toughness and attrition resistance required for use in industrial fluid bed or transport reactors. Accordingly, it would be desirable to have a selective, direct oxidation of an aliphatic hydrocarbon, such as an alkane or monoolefin, to the corresponding unsaturated aliphatic hydrocarbons, specifically the diolefin. It would be more desirable if such an oxidation produced a high selectivity and high productivity of the diolefin and other olefins, and correspondingly low selectivities to deep oxidation products, such as carbon dioxide. Finally, it would be most desirable if the above-identified process could be accomplished with a catalyst of high attrition resistance so as to be useful in a commercial scale fluid bed or transport reactor.

SUMMARY OF THE INVENTION

In one aspect, this invention is a process of preparing an unsaturated aliphatic hydrocarbon comprising contacting an aliphatic hydrocarbon having at least three carbon atoms with a catalyst of this invention, described hereinafter. Under the reaction conditions of the process of this invention more unsaturated aliphatic hydrocarbons, such as diolefins, are formed in a selectivity of at least about 40 mole percent.

Advantageously, aliphatic hydrocarbons can be oxidized directly to more highly unsaturated aliphatic hydrocarbons by the process of this invention. Surprisingly, the process of this invention produces a high selectivity and high productivity of more highly unsaturated aliphatic hydrocarbons, especially diolefins. More surprisingly, the process of this invention produces low selectivities and low yields of undesirable deep oxidation products, such as carbon monoxide and carbon dioxide. Unexpectedly, butadiene can be produced directly from butane in high selectivity and high productivity by the process of this invention while maintaining low selectivities of deep oxidation products. For the purposes of this invention, the "productivity" is defined as the grams of desired product produced per gram catalyst per hour.

The unsaturated aliphatic hydrocarbons, such as monoolefins and diolefins, are useful as monomers or comonomers in the formation of polyolefins. Butadiene is also potentially useful as an intermediate in the preparation of styrene.

In another aspect, this invention is a molybdate catalyst composition containing reactive oxygen. The composition comprises a support component containing magnesium oxide and at least one aluminum oxide selected from the group consisting of alumina ($Al_2O_3$) and magnesium aluminate ($MgAl_2O_4$). The support is further characterized as having a $MgO/Al_2O_3$ weight ratio in the range from about 0.30 to about 4.0 and a surface area of at least about 25 $m^2/g$. The catalyst composition also comprises a catalyst component consisting essentially of a molybdenum oxide, a magnesium oxide, and a promoting amount of an alkali metal promoter. Optionally, the catalyst may contain an oxide of vanadium. In preferred embodiments, the catalyst of this invention has an attrition number, defined hereinafter, less than 5 weight percent per hour.

The catalyst composition of this invention is useful in the above-identified process of oxidizing aliphatic hydrocarbons to more unsaturated aliphatic hydrocarbons. Advantageously, in its preferred forms the catalyst composition of this invention has improved attrition resistance when compared to the catalysts of the prior art; thus, the catalyst of this invention is useful in commercial fluid bed and transport reactors, such as riser reactors.

DETAILED DESCRIPTION OF THE INVENTION

The aliphatic hydrocarbons which can be employed in the process of this invention include alkanes and olefins which have three or more carbon atoms.

The alkanes can be alternatively described as paraffin hydrocarbons. These compounds are known to those skilled in the art as saturated hydrocarbons. As noted hereinbefore, the alkanes contain at least three carbon atoms, and additionally, can have straight-chain or branched structures. Typically, the alkane contains up to about 20 carbon atoms. Examples of suitable alkanes include n-butane, n-pentane, n-hexane, n-heptane, n-octane, n-nonane, n-decane, n-dodecane, and higher saturated homologues, as well as isobutane, isopentane, neopentane, and likewise branched hexanes, heptanes, octanes, nonanes, decanes, dodecanes, and higher branched homologues. Certain alicyclic hydrocarbons are suitable reactants, and therefore, for the purposes of this invention are included herein. Some examples of alicyclic hydrocarbons include cyclobutane, cyclopentane, cyclohexane, cycloheptane, cyclooctane, methylcyclopentane, methylcyclohexane and other alkyl-substituted cycloalkanes. Preferably, the alkane is normal or linear.

The olefins can be further described as aliphatic hydrocarbons containing at least one unsaturated double bond. As noted earlier, the olefins should also contain at least three carbon atoms, and typically up to about 20 carbon atoms. The location of the double bond is not critical; therefore, the double bond can occur at a terminal or internal location along the carbon chain. Preferably, however, the olefin has a normal or linear structure, rather than a branched structure. For example, 1-butene is preferred over isobutylene. Thus, some examples of suitable olefins include, 1-butene, 2-butene, 1-pentene, 2-pentene, 3-pentene, 1-hexene, 2-hexene, 3-hexene, and likewise 1-heptene, 1-octene, 1-nonene, 1-decene, and isomers thereof wherein the unsaturation occurs at any other position along the carbon chain. Olefins containing more than one double bond, such as 1,3-hexadiene and isoprene, are also acceptable, being converted in the process of this invention to more highly unsaturated hydrocarbons. Certain alicyclic olefins, such as cyclohexene and vinylcyclohexane, are also suitable starting materials, and therefore, for the purposes of this invention are included herein. Preferably, the olefin is a monoolefin. More preferably, the olefin is 1- or 2-butene. Alkynes, however, are not suitable reactants for the process of this invention.

The many specific examples of aliphatic hydrocarbons, noted hereinabove, are representative of those which are suitable for the process of this invention, and are not intended to be limiting thereof. Other aliphatic hydrocarbons may be available to one skilled in the art and may also be suitable for the process of the invention.

The preferred alkanes are normal paraffins which can be represented by the general formula:

$$CH_3—(CH_2)_n—CH_3$$

wherein n is an integer from 1 to 8. More preferably, n is an integer from 2 to 6. Most preferably, n is 2, and the alkane is n-butane.

Optionally, the aliphatic hydrocarbon reactant can be diluted with a non-reactive gas, such as nitrogen, helium, argon, methane, carbon dioxide or steam. While the type of diluent is determined by prevailing economic considerations, a preferable diluent is nitrogen. If a diluent is used, the amount can vary widely depending upon the design of the reactor and the capacity of the solid oxidant. The hydrocarbon content of the hydrocarbon-diluent mixture typically ranges from 1 mole percent to 100 mole percent. Preferably, the hydrocarbon content of the mixture ranges from about 10 mole percent to about 100 mole percent, more preferably, from about 40 mole percent to about 100 mole percent.

The catalyst composition of this invention, described in detail hereinbelow, is a solid heterogeneous oxide at least a portion of the oxygen of which is reactive. By this it is meant that a labile form of oxygen is present in the catalyst, and that this labile form of oxygen is capable of oxidizing the aliphatic hydrocarbon. Thus, in one aspect the catalyst of this invention is a solid oxidant. After the labile oxygen is removed through reaction, the catalyst is spent. Moreover, the catalyst may build up over time a carbonaceous residue on its surface. The spent and poisoned catalyst can be regenerated by contact with a source of gaseous oxygen. Thus, in addition to the aliphatic hydrocarbon, oxygen is required for the catalytic process of this invention.

Oxygen is typically supplied from a gaseous source provided as a continuous oxygen-containing feed. Any source of oxygen is acceptable, such as pure gaseous elemental oxygen, air, or nitrous oxide. The preferred source of oxygen is gaseous air. Optionally, the gaseous elemental oxygen can be diluted with a non-reactive gas, such as nitrogen, helium, argon, or carbon dioxide. Preferably, the diluent is nitrogen. If a non-reactive diluent is employed, the oxygen content of the mixture is preferably not greater than about 50 mole percent. More preferably, the oxygen content of the mixture ranges from about 0.5 mole percent to about 30 mole percent. Most preferably, the oxygen content of the mixture ranges from about 1 mole percent to about 20 mole percent.

The amount of oxygen employed in the catalytic process of this invention is any amount which is (1) sufficient to oxidize fully the solid heterogeneous catalyst, and (2) sufficient to remove carbonaceous residues from the catalyst's surface. Preferably, the regeneration of the catalyst is carried out separately from the oxidation of the aliphatic hydrocarbon.

Alternatively, it is acceptable to co-feed a small amount of gaseous elemental oxygen with the aliphatic hydrocarbon. The function of the co-feed is to burn off carbonaceous residues on the surface of the catalyst, to replenish to some extent the reactive oxygen of the catalyst, and to burn off any hydrogen which is formed in the process. The concentration of oxygen in the aliphatic hydrocarbon and oxygen feed is limited by the explosive limits of this mixture. Preferably, the oxygen concentration is maintained outside the lower explosive limit.

The molybdate catalyst composition of this invention comprises a support component and a catalyst component. The support contains magnesium oxide and at least one aluminum oxide selected from the group consisting of alumina ($Al_2O_3$) and magnesium aluminate spinel ($MgAl_2O_4$). The support has a $MgO/Al_2O_3$ weight ratio in the range from about 0.30 to about 4.0 and a surface area of at least about 25 $m^2/g$. The catalyst component consists essentially of an oxide of molybdenum, an oxide of magnesium, and a promoting amount of an alkali metal promoter. Optionally, the catalyst may contain an oxide of vanadium.

The aluminum oxide primarily imparts hardness and attrition resistance to the catalyst particles, so that they might be more suitable for use in fluid bed or transport reactors. Any source of aluminum oxide is acceptable, including $\alpha$-, $\beta$-, and $\gamma$-aluminas, hydrated alumina, such as boehmite alumina, aqueous colloidal alumina, stoichiometric $Al(OH)_3$, and aluminum alkoxides, as noted hereinbelow. Magnesium aluminate and magnesium aluminate hydroxides are also suitable sources of aluminum oxide. The magnesium oxide functions in a dual role: first, as a support for the catalyst components, and secondly, as a basic catalyst component which neutralizes the acidity of the alumina and other residual acid sites. It is highly desirable for the catalyst to be basic, because basicity enhances the desorption of olefinic products. Any source of magnesium oxide is acceptable; however, MgO is preferred. The molybdenum oxide contributes significantly to the catalyst's activity, especially as combined with magnesium oxide in the form of magnesium molybdate. Preferably, the molybdenum is in the +6 oxidation state. Any source of molybdenum oxide is acceptable, including for example, $MoO_3$, $(NH_4)_6Mo_7O_{24}\cdot4H_2O$, and $(NH_4)_2MoO_4$. The molybdenum oxide can also be obtained from a precursor molybdenum compound, such as molybdenum carbonyls, e.g., $Mo(CO)_6$. Preferably, the source of molybdenum oxide is ammonium heptamolybdate represented by the formula $(NH_4)_6Mo_7O_{24}\cdot4H_2O$. The alkali metal promoter functions to increase the basicity of the catalyst, thereby increasing the selectivity of higher unsaturates in the process of this invention. The alkali metal promoter is a Group IA metal compound. Small amounts of other elements may be present in the catalyst, provided that these elements do not materially change the performance of the catalyst.

It is noted that the support component may contain a spinel ($MgAl_2O_4$) phase. The weight percentage of spinel in the support component may range from 0 percent to about 100 percent.

Typically, the preparation of the catalyst begins with the combination of the magnesium oxide and aluminum oxide components to form a support for the other catalytic components. Any method of combination of these components is suitable; however, there are three preferred methods. The first method comprises impregnating a pre-formed spinel ($MgAl_2O_4$) with a solution containing a soluble magnesium salt, such as magnesium nitrate, magnesium chloride, magnesium sulfate, magnesium acetate or the like, provided that the salt can be converted to magnesium oxide on calcination; and thereafter calcining the impregnated spinel. The weight ratio of magnesia to magnesium aluminate can be conveniently expressed as a weight ratio of magnesia to alumina. This ratio is critical to the performance of the catalyst composition and is discussed separately hereinbelow. The temperature of calcination typically ranges from about 400° C. to about 1200° C., preferably, from about 450° C. to about 900° C., more preferably, from about 500° C. to about 700° C. The calcination is conducted for a time sufficient to form a fused composite which can function as a support for the catalytic components, but at least about 0.5 hour.

The second method involves impregnating a pre-formed alumina with a solution of a soluble magnesium salt, such as those identified hereinabove. Pre-formed aluminas are defined herein as anhydrous or hydrated solid aluminas, of which $\alpha$-, $\beta$-, and $\gamma$-aluminas and boehmite alumina are typical examples. The weight ratio of magnesia to alumina, $MgO/Al_2O_3$, is a critical parameter which is discussed in detail hereinbelow. The temperature of calcination typically ranges from about 400° C. to about 1200° C., preferably, from about 450° C. to about 900° C., mare preferably, from about 500° C. to about 700° C. The calcination is conducted for a time sufficient to form a fused and hardened composite which can function as a support for the catalytic components. Typically, the calcination is conducted for at least about 0.5 hour. During calcination a portion of the alumina and magnesia may chemically combine to form a spinel phase, $MgAl_2O_4$, which is intimately mixed between the domains of magnesia and alumina.

The third method of preparing the support comprises adding colloidal alumina to magnesium oxide and drying the resulting mixture under conditions sufficient to prepare a magnesia-alumina support. Colloidal alumina is an acidified aqueous suspension of hydrated aluminum oxide, wherein the particle surface area is so much greater than its volume that the particles are not settled out by gravity. A quantity of colloidal alumina suspension is added to the magnesia such that the final magnesia to alumina weight ratio falls within the range specified hereinafter. The pH of the colloidal alumina and magnesia mixture is about 9. The mixture is dried by any one of a variety of techniques, including aging and evaporating spray-drying, mash drying, tunnel drying, drum drying and the like. One preferred method involves aging and evaporating the mixture over a hot plate or equivalent heating means to form a thicker gel and eventually a hard solid mass, which is crushed and sieved to the desired particle size. The temperature of the aging and evaporation process is any which is compatible with the solvent system. Since the preferred solvent system is water, the temperature is in the range from about 30° C. to about 100° C. Preferably, the temperature is in the range from about 50° C. to about 90° C., more preferably, in the range from about 60° C. to about 80° C. The time required for aging will depend on the quantity of gel, and is any time sufficient to obtain the solid, hard mass.

For industrial scale applications the mixture containing magnesia and colloidal alumina, prepared hereinabove, is preferably spray dried rather than aged. Any spray drying equipment which is conventionally used to produce catalyst particles suitable for use in fluidized bed reactors may be employed. For example, a Niro Atomizer S-12.5-R/N spray drying apparatus is acceptable. Such an apparatus has a means for controlling the inlet and outlet temperature. Typically, the powder particles obtained by spray drying are spheroidal in shape, range in diameter from about 10 $\mu$m to about 250 $\mu$m, and exhibit excellent flow properties.

The powder which is obtained on aging or spray drying is calcined to yield a composite support consisting essentially of magnesia and alumina, and optionally, a spinel phase of magnesium aluminate. The calcination is conducted under conditions sufficient to fuse the alumina and magnesia into a hardened mass. Generally, the calcination is conducted at a temperature in the range from about 400° C. to about 1200° C. More preferably, the calcination temperature is in the range from about 450° C. to about 900° C., most preferably in the range from about 500° C. to about 700° C. Generally, the period of calcination depends upon the amount of material to be calcined, but lasts at least for about 0.5 hour.

The support component of this invention contains any weight ratio of magnesia to alumina provided that a support of sufficient hardness and basicity is obtained. Note that although the spinel phase exists as a distinct composition of $MgAl_2O_4$, a $MgO/Al_2O_3$ weight ratio is still calculable. Generally, the $MgO/Al_2O_3$ weight ratio is maintained in the range from about 0.1 to about 9.0, but ratios in the range from about 0.3 to about 4.0 are preferred. More preferred are weight ratios in the range from about 0.3 to about 2.0. Most preferred are weight ratios in the range from about 0.38 to about 0.80. Below the preferred lower ratio there may be too little magnesia and the catalyst may be too acidic. Above the preferred upper ratio there may be too much magnesia and the catalyst may lack attrition resistance and toughness.

The support component of this invention is further characterized by its surface area. Typically, the surface area is at least about 25 $m^2/g$. Preferably the surface area is at least about 35 $m^2/g$, more preferably, at least about 50 $m^2/g$. Even more preferably, the surface area ranges from about 50 $m^2/g$ to about 250 $m^2/g$, most preferably, from about 80 $m^2/g$ to about 170 $m^2/g$. It is well-known among those skilled in the art that low surface area is generally correlated with low catalytic activity; whereas high surface area is generally correlated with high catalytic activity. The catalyst composition of this invention exhibits both high surface area and high catalytic activity.

After the support component is prepared, the catalytic elements of molybdenum oxide, alkali metal promoter and, optionally vanadium oxide, are applied to the support. Provided that the $MgO/Al_2O_3$ weight ratio is adjusted within the suitable range identified hereinabove, there is no further need to add more magnesium oxide. Generally, the desired quantity of a molybdenum oxide or precursor compound, such as ammonium heptamolybdate or molybdenum carbonyl, is dissolved in a solvent to make a solution. Preferably, the molybdenum compound is ammonium heptamolybdate, and the solvent is water. The solution is brought into contact with the support composite, prepared hereinabove, and the resulting slurry is dried to remove solvent. If the solution is aqueous, the drying is conducted in an oven at a temperature in the range from about 70° C. to about 120° C. The dried slurry is thereafter calcined to form a catalytically active composition containing an aluminum oxide, magnesium oxide and molybdenum oxide. The calcination is typically conducted at a temperature ranging from about 300° C. to about 900° C. for a time ranging from 0.5 hour to about 24 hours. Preferably, calcination is conducted at a temperature in the range from about 500° C. to about 800° C., more preferably, from about 550° C. to about 650° C. Alternatively, the dried slurry, described hereinabove, can be employed directly with no prior calcination in the catalytic process of this invention. Since the molybdenum precursor can be converted into molybdenum oxide at or about 300° C., and since the catalyst bed is heated to a temperature higher than about 300° C., the dried composition will be converted in situ into a catalytically active aluminum oxide-magnesium oxide-molybdenum oxide mixture.

The mixed oxide catalyst composition usually shows X-ray diffraction peaks characteristic of one or more of the following: magnesium oxide, magnesium molybdate, magnesium aluminate spinel and alumina. The elemental analysis of the calcined solid reveals a composition ranging from about 3 weight percent $MoO_3$ to about 50 weight percent $MoO_3$ and from about 90 weight percent MgO to about 10 weight percent MgO with the balance being alumina. Preferably, the composition ranges from about 10 weight percent $MoO_3$ to about 30 weight percent $MoO_3$ and from about 60 weight percent MgO to about 20 weight percent MgO; more preferably, from about 12 weight percent $MoO_3$ to about 25 weight percent $MoO_3$ and from about 40 weight percent MgO to about 25 weight percent MgO.

It is required to add to the supported catalyst described hereinbefore a promoting amount of at least one alkali metal promoter. The promoter serves to increase the selectivity and productivity of unsaturated products, e.g. diolefins, in the process of this invention. Such a promoter is typically a compound of lithium, sodium, potassium, rubidium, cesium or francium of sufficient basicity to improve the selectivity to higher unsaturates in the process of this invention. Suitable compounds include the alkali oxides, hydroxides and carbonates. Compounds which decompose on heating to the oxides are also suitable, such as alkali metal acetates and oxalates. Alkali metal salts may be found which are also suitable, although typically, the alkali metal halides and alkali metal silicates are not preferred due to their lower basicity. Preferably, the alkali metal promoter is an alkali metal oxide, hydroxide, carbonate, acetate, or oxalate. More preferably, the alkali metal promoter is an oxide or hydroxide of potassium or cesium. Most preferably, the alkali metal promoter is an oxide or hydroxide of potassium.

The amount of alkali metal promoter is critical to the performance of the catalyst. Generally, any amount of alkali metal promoter is acceptable which is sufficient to increase the selectivity and the productivity of unsaturated products, such as diolefins, in the process of this invention. Typically, the amount of alkali metal promoter calculated as the alkali hydroxide is in the range from about 0.05 weight percent to about 5 weight percent based on the total weight of the aluminum, magnesium and molybdenum oxides. Preferably, the amount of alkali metal promoter calculated as the alkali metal hydroxide is in the range from about 0.1 weight percent to about 2 weight percent based on the total weight of the magnesium, aluminum and molybdenum oxides, more preferably, in the range from about 0.3 weight percent to about 1.5 weight percent. Below the lower preferred amount of alkali metal promoter the selectivity to diolefin is reduced while the selectivity to deep oxidation products is increased. Above the upper preferred amount of alkali metal promoter the selectivity and productivity to diolefin are also reduced.

The alkali metal promoter can be added to the molybdate catalyst in a variety of ways known to those in the art. For example, the promoter can be applied by the well-known impregnation technique, described for example by Charles N. Satterfield in *Heterogeneous Catalysis in Practice*, McGraw-Hill Book Company, New York, 1980, pp. 82-83, incorporated herein by reference. In this technique the molybdenum-impregnated support is immersed in a solution of the alkali metal promoter, for example, a methanolic solution of the alkali metal oxide or hydroxide. The alkali-impregnated support is then drained of excess solution, dried in an oven to remove residual solvent, and calcined at a temperature in the range from about 550° C. to about 650° C. Alternatively, the alkali metal promoter can be impregnated onto the support by the incipient wetness technique, such that the pores are filled with solution of the alkali metal oxide or hydroxide but essentially no excess solution is used. The impregnated support thus prepared is also dried in an oven to remove solvent. As a further alternative the molybdenum compound can be impregnated from the same solution as the alkali metal compound.

Optionally, the molybdate catalyst of this invention can contain an activator which functions to increase the activity of the catalyst at any given temperature. Preferably, the activator does not decrease significantly the selectivity to diolefins and monoolefins. Preferably, the activator allows the reaction to be run at a lower temperature, while achieving high selectivity and high productivity of diolefins. Activators which are suitable for incorporation into the catalyst include the oxides of vanadium, preferably $V_2O_5$. Any amount of vanadium oxide can be added to the catalyst provided that (1) the activity of the catalyst is increased, and (2) the selectivity for alkenes, including mono- and diolefins, is not significantly decreased. Generally, if an activator is used, the concentration ranges from about 0.05 weight percent to about 10 weight percent based on the total weight of the catalyst. Preferably, the concentration of activator ranges from about 0.1 weight percent to about 5 weight percent, more preferably, from about 0.15 weight percent to about 1.5 weight percent. The activator can be incorporated into the support and molybdenum oxide slurry prior to calcination, or can be applied to the calcined aluminum-magnesium-molybdenum oxides by the impregnation technique, described hereinbefore.

The preferred commercial reactor for the process of this invention is a transport bed reactor, such as a riser reactor. In such reactors the catalyst particles are subjected to constant impact with other catalyst particles and with the walls of the reactor. Such forces gradually reduce the size of the catalyst particles to small fines which are lost in the reaction products; thus, the useful lifetime of the catalyst is greatly limited. Consequently, it is required for the catalyst to be prepared in a form which is able to withstand high impact and erosion forces. A butane oxidation catalyst comprising magnesium molybdate supported on magnesia does not possess the attrition resistance required for commercial use. In contrast, the alkali-promoted magnesium molybdate catalyst of this invention supported on the preferred composites described hereinbefore typically possesses the attrition resistance required for commercial use.

It is believed that the weakness of a catalyst comprising magnesium molybdate supported on magnesia is directly related to the high sintering temperature of magnesium oxide and the absence of strong intermolecular linkages. The sintering temperature is so much higher than normal calcination temperatures and normal operating temperatures of the process of this invention that the particles do not have the opportunity to fuse and bind together. One means of strengthening the magnesium molybdate catalyst is to incorporate into the catalyst a support component. Preferably, the component is a high surface area, attrition resistant composite of magnesia and alumina, optionally containing a magnesium aluminate spinel phase, as described hereinabove. It is believed that the alumina imparts hardness to the catalyst, while the magnesia and/or magnesium aluminate reduces the natural acidity of the alumina. Such a theory, however, should not be binding or limiting of the inventions disclosed herein. Suitable methods of testing attrition resistance are described in the section on Illustrative Embodiments hereinafter.

Another important property of the catalyst of this invention is its particle size. The prior art usually teaches the use of small spheroidal catalyst particles for fixed bed and transport fluid bed reactors. Such particles usually range from 20 $\mu$m to 200 $\mu$m in diameter, preferably from 80 $\mu$m to 120 $\mu$m in diameter. Surprisingly, we have found that spheroidal, meaning approximately spherical, particles in the range from about 200

μm to about 1700 μm in diameter exhibit improved performance in transport reactors. Preferably, the particles are in the range from about 500 μm to about 1200 μm, more preferably from about 600 μm to about 1000 μm. The larger particles of our invention exhibit less "caking" and therefore give a smoother low velocity flow. Also, our larger particles exhibit lower pressure drop in the dense phase sections of the reactor, less violent particle-wall collisions, and the ability to better differentiate between the gas residence time and the catalyst residence time.

The process of this invention can be carried out in any suitable reactor, including batch reactors, continuous fixed-bed reactors, slurry reactors, fluidized bed reactors, and riser reactors. Preferably, the reactor is a continuous flow reactor, such as a continuous fixed-bed reactor or a riser reactor of the type described hereinafter.

Typically, the riser reactor comprises an upright vessel of relatively low ratio of diameter to length. The catalyst is continuously charged into the bottom of the riser reactor. Likewise, the aliphatic hydrocarbon feedstream is delivered concurrently to the bottom of the riser reactor as a vapor phase feed or as a liquid phase feed. Preferably, the alkane is delivered as a vapor phase feed pre-mixed with an inert, gaseous diluent, and optionally, a small concentration of oxygen. The feed moves upward through the reactor, thereby contacting the catalyst. Upon contacting the catalyst, the feed is converted into a mixture of products, including monoolefins, diolefins, higher unsaturated olefins, cracking products, deep oxidation products, such as carbon monoxide and carbon dioxide, and heavies, such as benzene and furan in the case of a butane feed. The product stream exits the riser reactor and is separated by known methods, such as distillation, to recover the desired products, typically the diolefins. Unreacted alkanes and monoolefin products are recycled to the riser reactor for further oxidation.

Riser reactor technology is advantageous for the process of this invention, because (1) the hazard of using a feedstream containing a mixture of alkane and/or olefin and elemental oxygen is eliminated, and (2) the selectivity for diolefins is enhanced, especially at the high temperatures required for this process. In contrast, if a feedstream of alkane and oxygen is employed at a high temperature and a high oxygen/alkane mole ratio, there is a tendency to produce more deep oxidation products, such as carbon monoxide and carbon dioxide. In addition, the danger of a run-away reaction is greater.

The operation of a riser reactor can be simulated by employing a method of alternating pulses. Thus, a pulse of the hydrocarbon-containing feed is passed through the catalyst bed where it is oxidized to form the desired olefin products. Next, a pulse of inert gas is passed through the catalyst bed to purge the bed of residual alkanes and alkenes. After purging, a pulse of oxygen-containing feed is passed through the catalyst bed to regenerate the catalyst. Finally, a second pulse of inert gas is passed through the catalyst bed to pure the bed of oxygen, after which the cycle is repeated. Such a procedure is employed in the illustrative embodiments, described hereinafter.

The aliphatic hydrocarbon reactant is contacted with the catalyst at any operable temperature which promotes the oxidation process of this invention and yields the desired unsaturated products. Typically, the temperature is in the range from about 400° C. to about 700° C. Preferably, the temperature is in the range from about 500° C. to about 650° C. More preferably, the temperature is in the range from about 530° C. to about 600° C. Below the preferred lower temperature the conversion of reactant may be low. Above the preferred upper temperature the selectivity and productivity of diolefin products may decrease.

Likewise, the aliphatic hydrocarbon reactant is contacted with the catalyst at any operable pressure which promotes the oxidation process of this invention and yields the desired unsaturated products. Typically, the partial pressure of the reactant is adjusted to maintain the reactant in the vapor state at the operating temperature. Preferably, the partial pressure of the aliphatic hydrocarbon is in the range from about subatmospheric to about 100 psig. More preferably, the partial pressure is in the range from about 1 psig to about 30 psig. Most preferably, the partial pressure is in the range from about 3 psig to about 15 psig.

When the process of this invention is conducted in a continuous flow reactor, described hereinbefore, the flow rate of the reactants can be varied. Generally, in the process of this invention the aliphatic hydrocarbon reactant is fed into the reactor at any operable flow rate which promotes the oxidation reaction and yields the desired conversion and selectivity of unsaturated products. The flow rate is expressed as the gas hourly space velocity (GHSV) and is given in units of volume of aliphatic hydrocarbon-containing gaseous feed per total reactor volume per hour or simply $hr^{-1}$. Typical values vary from about 100 $hr^{-1}$ to about 20,000 $hr^{-1}$. It should be understood that the space velocity controls the residence time of the reactants. In a riser reactor, for example, a gas residence time less than about 10 seconds is preferred, while times less than about 5 seconds are more preferred and less than about 1 second are most preferred.

For the case of the riser reactor, after contacting the catalyst with the aliphatic hydrocarbon reactant the spent catalyst leaves the top of the reactor and is transported into a second reactor for regeneration. Regeneration is effected by contact with oxygen. Typically, a preheated oxygen source, like that described hereinbefore, is fed into the bottom of the second reactor. The spent catalyst is contacted with the oxygen source at any operable temperature, pressure, and oxygen-source flow rate which are sufficient to regenerate the catalyst. The process variables should be controlled, however, so as to prevent a runaway reaction or the buildup of excessive heat. Preferably, the temperature is in the range from about 500° C. to about 700° C., more preferably, in the range from about 550° C. to about 650° C. Preferably, the pressure is in the range from subatmospheric to about 100 psig, more preferably, in the range from about 2 psig to about 50 psig. The oxygen-source flow rate required will depend upon the heat transfer properties of the particular reactor. For example, at some high flow rates the temperature may rise dramatically resulting in an uncontrolled reaction.

When the aliphatic hydrocarbon is contacted with the catalyst of this invention, an oxidation of the aliphatic hydrocarbon occurs resulting in the loss of at least two hydrogen atoms from the hydrocarbon reactant with formation of by-product water. The organic products which are produced are predominantly unsaturated aliphatic hydrocarbons, such as monoolefins and diolefins. These unsaturated products usually contain the same number of carbon atoms as the reactant aliphatic hydrocarbon. Thus, these products are not products of cracking, which would contain fewer carbon atoms than the starting hydrocarbon. Generally, also, the unsaturated products possess a higher degree of unsaturation than the reactant hydrocarbon. For example, alkanes, such as butane, can lose two hydrogen atoms to yield monoolefins, such as 1-butene, trans-2-butene, and cis-2-butene. In turn, monoolefins, such as the butenes previously cited, can lose two hydrogen atoms to form 1,3-butadiene.

The preferred diolefin products can be represented by the general formula:

$$CH_2=CH-CH=CH-(CH_2)_m-H$$

wherein m is an integer from 0 to about 6. Preferably, m is an integer from 0 to about 2. More preferably, m is 0 and the unsaturated product is 1,3-butadiene. Isomers of the formula shown hereinabove can also be formed wherein the unsaturation occurs at any other location along the carbon chain. Preferably, the unsaturation occurs in a conjugated fashion, as exemplified in the product 1,3-butadiene. Even more unsaturated variants of the general formula can be formed wherein further oxidation has occurred to yield more than two ethylenic double bonds. Alkynes, however, are not formed in significant amounts.

In addition to alkenes, the product stream can contain by-products of various types. For example, when the saturated alkane is n-butane, small quantities of cracking products, such as propylene and ethylene, can be formed, as well as heavies, such as benzene and furan, and deep oxidation products, such as carbon monoxide and carbon dioxide. Unexpectedly, however, these by-products, especially the deep oxidation products, are significantly reduced over the prior art processes.

For the purposes of this invention, "conversion" is defined as the mole percentage of aliphatic hydrocarbon reactant lost from the feed stream as a result of reaction. The conversion can vary widely depending upon the reactants., the form of the catalyst, and the process conditions such as temperature, pressure, flow rate, and catalyst residence time. Within the preferred temperature range, as the temperature increases the conversion generally increases. Within the preferred gas hourly space velocity range, as the space velocity increases the conversion generally decreases. Typically, the conversion of the aliphatic hydrocarbon is at least about 10 mole percent. Preferably, the conversion is at least about 20 mole percent; more preferably, at least about 30 mole percent; even more preferably, at least about 40 mole percent; and most preferably, at least about 50 mole percent.

Likewise, for the purposes of this invention "selectivity" is defined as the mole percentage of converted carbon which forms a particular product. Typically, selectivities also vary widely depending upon the reactants, the form of the catalyst, and the process conditions. Typically, the process of this invention achieves high selectivities to diolefins. Within the preferred temperature range, as the temperature increases the selectivity for alkenes generally decreases. Within the preferred space velocity range, as the space velocity increases the selectivity for alkenes generally increases. Preferably, the combined selectivity to all alkenes is at least about 50 mole percent; more preferably, at least about 60 mole percent; even more preferably, at least about 70 mole percent; most preferably, at least about 80 mole percent. Typically, the selectivity to diolefins is at least about 40 mole percent. Preferably, the selectivity to diolefins is at Least about 50 mole percent, more preferably, at least about 60 mole percent, most preferably, at least about 70 mole percent.

The concept of simultaneous high conversion and high selectivity can be conveniently expressed in terms of yield. For the purposes of this invention, the term "yield" refers to the numerical product of the single-pass conversion and selectivity. For example, a process according to the present invention operating at a conversion of 0.65, or 65 mole percent, and a selectivity to diolefin of 0.75, or 75 mole percent, would have a diolefin yield of 0.49, or 49 mole percent. Typically, the yield of diolefin achieved in the process of this invention is at least about 8 mole percent. Preferably, the yield of diolefin achieved in the process of this invention is at least about 18 mole percent, more preferably at least about 28 mole percent, Most preferably, at least about 35 mole percent. Typically, in the oxidation of butane the yield of total $C_4$ olefins is at least about 25 mole percent. Preferably, in the oxidation of butane the yield of total $C_4$ olefins is at least about 30 mole percent, more preferably, at least about 35 mole percent, most preferably, at least about 40 mole percent.

The rate at which a desired product is produced in the process of this invention can be expressed in the concept of space-time yield. For the purposes of this invention the "space-time yield" is defined as the mole percentage yield of a given product per hour (yield $hr^{-1}$), and it is the numerical product of the single-pass conversion, the selectivity, the gas hourly space velocity, and the concentration of the aliphatic hydrocarbon in the feedstream, wherein the conversion, selectivity and concentration are expressed as decimal fractions. Preferably, the space-time yield of diolefin in the process of this invention is at least about 30 percent per hour, more preferably, at least about 120 percent per hour, and most preferably, at least about 200 percent per hour.

Another measure of the rate at which a desired product is produced is the "productivity," defined as the grams desired product formed per gram catalyst per hour (g/g cat-hr). Preferably, the productivity of butadiene in this process is at least about 0.2 g/g cat-hr, more preferably, at least about 0.4 g/g cat-hr, and most preferably, at least about 0.5 g/g cat-hr. Preferably, the productivity of combined $C_4$ olefins in this process is at least about 0.3 g/g cat-hr, more preferably, at least about 0.4 g/g cat-hr, most preferably, at least about 0.9 g/g cat-hr.

ILLUSTRATIVE EMBODIMENTS

Testing the attrition resistance of a catalyst requires having on hand a large amount of catalyst sample. It would be desirable to have a simple test procedure for small catalyst samples which gives an indication of attrition resistance. A test of crush strength is such a procedure, because increased crush strength indicates better attrition resistance. Crush strength can be tested on any conventional equipment employed for such a purpose, for example, an Instron Model 1125. Generally, the catalyst is sized into 8-mesh granules which are calcined at 600° C. for 2 hours, and thereafter the crush strength is determined. Usually the crush strength of the preferred catalysts of this invention is at least about 5 lb, preferably, at least about 10 lb, more preferably, at least about 15 lb.

The actual attrition resistance of the preferred catalyst of this invention can be tested on any conventional equipment intended for such a purpose. A suitable testing apparatus is comprised of a stainless steel standpipe of ½ inch diameter and about 30 inches length, which is joined through a "J" valve to a riser tube of similar diameter and about 52 inches length. A 3-inch diameter stainless steel cyclone is attached to the riser tube at the cyclone entrance port and to the standpipe at the cyclone exit port, thereby creating a circulation loop wherein gas-solid separation is effected and the solids are returned to the standpipe. Normally, the material to be tested is charged into the system and is fluidized by the introduction of a gas at a flow rate from about 0.1 l s$^{-1}$ to about 1.0 l s$^{-1}$ at the "J" valve. The entrained powder moves in the upward gas stream and is recirculated upon separation by gravity in the cyclone recovery system. Typically, samples are taken periodically up to a total test time of about 15 hours. The amount of fines generated per unit time is determined and an attrition number is calculated by comparison to the initial coarse fraction. Preferably, the attrition number of the catalyst of this invention is less than about 5 weight percent per hr (wt. percent hr$^{-1}$), preferably, less than about 1 wt. percent hr$^{-1}$.

The following examples are illustrative of the process and catalyst of this invention, but are not intended to be limiting thereof. All percentages are given in mole percent carbon, unless noted otherwise.

EXAMPLES 1 (a-b)

Catalyst Preparation (a) Magnesium oxide powder (17 g, Magox Premium Grade MgO) is dispersed in deionized water (96 g) using a high shear disperser. To the resulting slurry is gradually added 20 weight percent alumina colloid (200 g, Nyacol) to form a viscous mixture comprising 30 weight percent MgO and 70 weight percent Al$_2$O$_3$. An additional 52 g of water is added to provide a manageable rheology. The mixture is aged and gelled by heating on a hot plate with stirring at 70° C. for about 2 hours to yield a hard white solid. The white solid is crushed and heated over a 4-hour period to 600° C. and calcined at 600° C. for 4 additional hours resulting in a spinel composite support having a MgO/Al$_2$O$_3$ weight ratio of 0.43 and a surface area of 169 m$^2$/g. The X-ray diffraction spectrum of the support displays reflections which can be attributed to crystalline MgO, as well as spinel and alumina. The support is tested on an Instron Model 1125 and is found to have an average crush strength of 15 pounds.

(b) A spinel composite support is prepared according to the procedure of Example 1 with the exception that 44 g of magnesium oxide powder, 280 g of alumina colloid and 249 g of deionized water are employed. The resulting composite support has a MgO/Al$_2$O$_3$ weight ratio of 0.78 and a surface area of 163 m$^2$/g. The X-ray diffraction spectrum of the support exhibits reflections which can be attributed to crystalline MgO, as well as spinel and alumina.

The spinel composite support (20 g), prepared in (b) hereinabove, is impregnated to incipient wetness with 20.44 g of a solution containing ammonium heptamolybdate (35.25 weight percent) and cesium hydroxide (1.85 weight percent). The impregnated support is dried at 125° C. for 2 hours, heated up to 600° C. over a period of 4 hours, and calcined at 600° C. for an additional 3 hours. The resulting catalyst (E1) contains 22.4 weight percent MoO$_3$ and 1.20 weight percent Cs$_2$O and has a surface area of 122 m$^2$/g.

EXAMPLE 2 (a-b)

Butane Oxidation

The catalyst of Example 1(b) (E1) is employed in the oxidation of butane in the following manner: approximately 15 cc of catalyst is loaded into a Vycor reactor tube (18 mm OD×7.6 cm length). The temperature of the reaction is measured from a stainless steel thermowell (⅛ inch OD) embedded in the catalyst sample. A feedstream containing butane (10-20 volume percent) and helium (90-80 volume percent) is passed over the catalyst for about 10-30 seconds. The flow of the feedstream is stopped and a purge stream comprising pure helium is passed over the catalyst at the same flow rate for 1 minute. The purge stream is stopped and a stream of oxygen (20 volume percent) in helium is passed over the catalyst at the same flow rate for 1 minute, followed by another purge stream of helium for 1 minute. This cycle is repeated and the combined products are collected in a Saran ® polyvinylidene chloride plastic bag for analysis. Analysis is performed on a Carle gas chromatograph designed to analyze for C$_1$-C$_5$ alkanes, alkenes and alkadienes, as well as permanent gases such as N$_2$, O$_2$, CO, CO$_2$, H$_2$, and heavier products including furan, benzene, and C$_6$ compounds. Isobutane is mixed with the feed or products as a standard. "Unknowns" are obtained from the difference between the carbon balance and 100 percent. The process conditions and results are set forth in Table I.

TABLE I①

| Example | 2a | 4a | 2b | 4b |
|---|---|---|---|---|
| Catalyst: | E1 | E3 | E1 | E3 |
| Weight % Cs$_2$O | 1.2 | 1.4 | 1.2 | 1.4 |
| T, °C. | 570 | 565 | 580 | 580 |
| GHSV, hr$^{-1}$ | 1084 | 1044 | 990 | 990 |
| % Conversion | 19.58 | 33.25 | 27.48 | 41.79 |
| % Selectivities: | | | | |
| 1-butene | 10.96 | 6.78 | 7.80 | 5.50 |
| tr-2-butene | 8.66 | 5.11 | 5.86 | 3.99 |
| cis-2-butene | 9.28 | 5.06 | 7.23 | 3.94 |
| butadiene | 63.60 | 66.71 | 68.46 | 64.98 |
| Sum C4's | 92.50 | 83.66 | 89.35 | 78.41 |
| propylene | 0.00 | 0.68 | 1.37 | 0.75 |
| ethylene | 3.40 | 2.99 | 3.57 | 4.01 |
| % Total Cracking | 3.40 | 3.67 | 4.94 | 4.76 |
| CO$_2$ | 4.10 | 9.18 | 4.86 | 10.91 |
| CO | 0.00 | 2.16 | 0.85 | 3.49 |
| % Deep Oxidation | 4.10 | 11.34 | 5.71 | 14.39 |
| furan/benzene | 0.00 | 1.33 | 0.00 | 1.95 |
| Unknown | 0.00 | 0.00 | 0.00 | 0.48 |
| % Total Heavies | 0.00 | 1.33 | 0.00 | 2.43 |
| Total C balance | 103.4 | 100.0 | 101.1 | 99.8 |
| g C$_4$/g cat-hr | 0.108 | 0.143 | 0.128 | 0.168 |
| % Yield C4's | 18.10 | 27.82 | 24.55 | 32.77 |

①Catalyst, 16 cc.

It is seen that the cesium-promoted magnesium molybdate catalyst supported on the magnesia alumina spinel composite catalyzes the oxidation of butane to butadiene and butene in high selectivity.

EXAMPLE 3

Catalyst Preparation

A magnesia alumina spinel composite support is prepared as is Example 1(b). The spinel composite (20 g) is impregnated to incipient wetness with 19.49 g of a solution containing cesium hydroxide (1.66 weight percent), ammonium vanadate (1.39 weight percent) and ammonium heptamolybdate (27.22 weight percent). The impregnated support is dried at 125° C. for 2 hours, heated to 600° C. over a period of 4 hours, and calcined at 600° C. for an additional 3 hours. The resulting catalyst (E3) contains 17.44 weight percent $MoO_3$, 0.85 weight percent $V_2O_5$ and 1.43 weight percent $Cs_2O$ and has a surface area after calcination of 122 m²/g.

EXAMPLES 4 (a-b)

Butane Oxidation

The catalyst prepared in Example 3 (E3) is employed in the oxidation of butane as described in Example 2. The process conditions and results are set forth in Table I. It is seen that the magnesium molybdate catalyst promoted with cesium and vanadium oxides and supported on the alumina magnesia spinel composite catalyzes the oxidation of butane to butadiene and butene in high selectivity.

EXAMPLE 5

Catalyst Preparation (a) Support preparation

Magnesium oxide powder (600 g) is dispersed in deionized water (5733 g) using a high shear disperser. To the resulting slurry is gradually added under low shear colloidal alumina (7000 g, 20 weight percent). The mixture, thus obtained, is spray dried using a nozzle atomizer having a 2-mm diameter orifice under a pressure of 40 psig. The inlet temperature of the nozzle is 300° C. and the outlet temperature is 120° C. A white powder with excellent flow properties is obtained from the spray drying. The powder is calcined at 600° C. for 2 hours to yield a composite support having a surface area of 184.3 m²/g and a $MgO/Al_2O_3$ weight ratio of 0.43. The X-ray diffraction spectrum of the support exhibits reflections which can be attributed to crystalline MgO as well as spinel and alumina phases. Calcining a portion of the powder for 4 hours longer at 800° C. reduced the surface area only slightly to 143.2 m²/g. The support, obtained by calcining the powder at 600° C., has an average particle size of about 60 μm. Examination of the particles by scanning electron microscopy shows the presence of spheroidal particulates which have excellent flow properties. The support is subjected to an attrition test in a circulating loop, as described hereinbefore at the beginning of the section entitled "Illustrative Embodiments", and an attrition number of 0.28 wt. percent hr$^{-1}$ is obtained. This value compares favorably with a commercial fluid catalytic cracker (FCC) alumina useful in transport reactors, which has an attrition number of 0.99 wt. percent hr$^{-1}$.

(b-d) Catalyst Examples

Magnesia alumina spinel supports are prepared as described in (a) hereinabove, with the exception that they contain sufficient MgO to give compositions of 40, 44 and 30 weight percent MgO and with the exception that they are not calcined. The supports are pressed at 5 Kpsig in an isostatic press, crushed to 20-80 mesh, and calcined at 600° C. or 5 hours. To 50 g of each support is added a solution containing ammonium heptamolybdate (33.23 weight percent), $K_2CO_3$ (0.62 weight percent) and hydrogen peroxide (2.5 weight percent of a 30 weight percent peroxide solution) neutralized to pH 9 with ammonium hydroxide. The impregnated supports (E-5-b-d) are dried at 110° C. for 18 hours and calcined at 600° C. for 3 hours to yield the catalysts. The amount of the solution applied to each support is given in Table II.

TABLE II[1]

| Catalyst | E-5b | E-5c | E-5d |
|---|---|---|---|
| Solution (g) | 49.9 | 47.00 | 46.40 |
| Wt % MgO[2] | 30 | 40 | 44 |
| Wt % $MoO_3$ | 21.20 | 20.23 | 20.03 |
| Wt % $K_2O$ | 0.33 | 0.32 | 0.31 |
| $MgO/Al_2O_3$ | 0.43 | 0.67 | 0.79 |
| % $C_4$ Conversion | 29.18 | 30.70 | 34.05 |
| % Selectivities: | | | |
| butenes | 19.39 | 17.84 | 16.38 |
| butadiene | 60.21 | 66.39 | 64.68 |
| Sum $C_4$'s | 79.60 | 84.23 | 81.07 |
| ethylene | 1.74 | 2.29 | 1.91 |
| $CO_2$ | 7.68 | 6.25 | 7.29 |
| CO | 2.79 | 2.32 | 2.80 |
| % Deep Oxidation | 10.47 | 8.58 | 10.09 |
| furan/benzene | 0.00 | 0.63 | 2.08 |
| Unknown | 8.19 | 4.28 | 4.85 |
| % Total Heavies | 8.19 | 4.91 | 6.93 |
| Total C balance | 97.61 | 98.69 | 98.35 |
| g $C_4$/g cat-hr | 0.136 | 0.161 | 0.176 |
| g BD/g cat hr[3] | 0.10 | 0.13 | 0.14 |

[1] Catalyst, 15 cc; T, 570° C.; GHSV, 844/hr.
[2] Wt. % before addition of $MoO_3$ and $K_2O$.
[3] BD = butadiene

EXAMPLE 6

Butane Oxidation

The catalysts prepared in Example 5 (E-5b-E-5d) are employed in the oxidation of butane as described in Example 2. The process conditions and results are set forth in Table II. It is seen that the potassium-promoted magnesium molybdate catalysts supported on the alumina magnesia spinel composite catalyze the oxidation of butane to butadiene and butene in high selectivity.

EXAMPLE 7

Catalyst Preparation

A spinel precursor is prepared by a known method of coprecipitating magnesium and aluminum hydroxides at pH 9 from an aqueous solution of magnesium and aluminum salts via the addition of NaOH and $Na_2CO_3$. The spinel precursor is calcined at 600° C. for 3 hours thereby forming a magnesium aluminate spinel ($MgAl_2O_4$). The pre-formed spinel is impregnated to incipient wetness with a 1.75 Molal aqueous solution of magnesium acetate tetahydrate (37 weight percent). The impregnated spinel is calcined for 3 hours at 600° C. to give a spinel composite containing an additional 17.1 weight percent MgO and a $MgO/Al_2O_3$ weight ratio of 0.69. Thereafter, the composite (16.3 g) is impregnated to incipient wetness with an aqueous solution (17.53 g) of ammonium heptamolybdate (26.5 weight percent), and then calcined at 600° C. for 4 hours. This material is further impregnated with a methanolic solution (8.5 g) of cesium hydroxide hydrate (0.63 weight percent) and recalcined at 600° C. for 3 hours. The resulting catalyst (E7) contains 18.8 weight percent $MoO_3$ and 0.25 weight percent $Cs_2O$ and has a surface area of 115 $m^2/g$.

EXAMPLE 8(a–b)

Butane Oxidation

The catalyst of Example 7 (E7) is employed in the oxidation of butane according to the procedure described in Example 2. The results are presented in Table III.

TABLE III[1]

| Example | 8a | 8b | CE 1a | CE 1b |
|---|---|---|---|---|
| Catalyst: | 7 | 7 | CE 1 | CE 1 |
| Weight % $Cs_2O$ | 0.240 | 0.240 | 0.00 | 0.00 |
| GHSV, g/ml hr | 150 | 150 | 600 | 600 |
| Temperature (°C.) | 570 | 550 | 570 | 550 |
| % Conversion | 37.91 | 25.70 | 48.08 | 33.82 |
| % Selectivities: | | | | |
| 1-butene | 4.76 | 7.04 | 3.08 | 4.16 |
| tr-2-butene | 4.48 | 7.15 | 3.15 | 5.00 |
| cis-2-butene | 4.25 | 5.95 | 2.29 | 4.33 |
| butadiene | 62.83 | 62.74 | 48.69 | 56.99 |
| Sum $C_4$'s | 76.32 | 82.88 | 57.21 | 70.47 |
| ethylene | 2.24 | 1.59 | 1.94 | 1.39 |
| % Total Cracking | 2.24 | 1.59 | 1.94 | 1.39 |
| $CO_2$ | 7.83 | 4.84 | 17.86 | 12.56 |
| CO | 3.53 | 2.26 | 8.83 | 6.33 |
| % Deep Oxidation | 11.37 | 7.10 | 26.68 | 18.89 |
| furan/benzene | 3.91 | 0.0 | 9.08 | 6.78 |
| Unknown | 9.84 | 12.09 | 7.94 | 5.79 |
| % Total Heavies | 13.75 | 12.09 | 17.01 | 12.57 |
| Total C balance | 97.66 | 97.83 | 97.55 | 99.19 |
| g $C_4$/g cat-hr | 0.045 | 0.033 | 0.042 | 0.037 |
| % Yield $C_4$'s | 28.93 | 21.30 | 27.50 | 23.83 |

[1]Catalyst, 15 cc.

It is seen that the cesium-promoted magnesium molybdate catalyst supported on the spinel composite catalyzes the oxidation of butane to butadiene and butene in high selectivity.

COMPARATIVE EXPERIMENT 1 (CE 1-a and CE 1-b)

A composition is prepared according to the procedure described hereinabove in Example 7, with the exception that no cesium hydroxide is impregnated into the catalyst. The composition is employed in the oxidation of butane according to the procedure described in Example 2. The results are presented in Table III. When Example 8 is compared with Comparative Experiment 1, it is seen that the catalyst of this invention containing low levels of cesium promoter achieves a higher selectivity to butadiene and butene and a lower selectivity to deep oxidation products than a similar catalyst which does not contain cesium promoter.

EXAMPLES 9 (a–e)

Catalyst Preparation

An aqueous solution (1184 g) containing 71.5 weight percent magnesium nitrate hexahydrate is added to porous alumina spheres (713.3 g; UOP. 700 μm ). The resulting slurry is dried for 18 hours at 150° C., and calcined by heating up to 460° C. over a 4-hour period, holding at 460° C. for 2 hours, heating further to 540° C. over a 2-hour period, and holding at 540° C. for 3 hours in flowing air. More of the magnesium nitrate solution (1186.9 g) is added to the dried alumina spheres, and the drying and calcination procedures are repeated. A composite support is obtained containing 27.7 weight percent MgO having a $MgO/Al_2O_3$ weight ratio of 0.38 and a surface area of 101 $m^2/g$.

Samples (35 g) of the composite are impregnated with a solution containing ammonium heptamolybdate and potassium carbonate as set forth in Table IV. The concentration of ammonium heptamolybdate varies in each solution, while the concentration of potassium carbonate is nearly constant. The impregnated composites are calcined at 600° C. for 4 hours to yield potassium-promoted molybdate catalysts (E9 a–e) supported on the magnesia, alumina spinel composite characterized in Table IV.

TABLE IV[1]

| Example | 10a | 10b | 10c | 10d | 10e |
|---|---|---|---|---|---|
| Catalyst: | 9a | 9b | 9c | 9d | 9e |
| Solution: | | | | | |
| % AHM[2] | 34.80 | 29.0 | 22.50 | 15.90 | 11.60 |
| % $K_2CO_3$ | 0.65 | 0.67 | 0.66 | 0.65 | 0.64 |
| Wt % $MoO_3$ | 24.30 | 21.90 | 16.20 | 11.40 | 8.40 |
| Wt % $K_2O$ | 0.38 | 0.42 | 0.40 | 0.39 | 0.39 |
| $MgO/Al_2O_3$ | 0.38 | 0.38 | 0.38 | 0.38 | 0.38 |
| % Conversion | 24.67 | 24.27 | 29.84 | 22.34 | 11.28 |
| % Selectivities: | | | | | |
| Sum butenes | 25.30 | 25.56 | 20.55 | 22.27 | 23.81 |
| Butadiene | 63.21 | 65.89 | 63.48 | 61.04 | 40.18 |
| Sum $C_4$'s | 88.51 | 91.45 | 84.03 | 83.31 | 64.00 |
| ethylene | 0.00 | 0.00 | 0.00 | 0.00 | 0.00 |
| $CO_2$ | 6.10 | 4.60 | 5.63 | 6.32 | 10.68 |
| CO | 2.79 | 0.00 | 2.14 | 1.86 | 2.51 |
| % Deep Oxidation | 8.89 | 4.60 | 7.77 | 8.19 | 13.19 |
| benzene/furan | 0.18 | 0.00 | 0.00 | 0.00 | 0.00 |
| Unknown | 0.15 | 1.21 | 5.89 | 2.69 | 8.13 |
| % Total Heavies | 0.33 | 1.21 | 5.89 | 2.69 | 8.13 |
| % C Balance | 99.96 | 99.71 | 98.24 | 99.40 | 99.08 |
| g $C_4$/g cat-hr | 0.11 | 0.11 | 0.13 | 0.10 | 0.04 |
| g BD/g cat-hr[2] | 0.09 | 0.08 | 0.10 | 0.08 | 0.03 |

[1]Catalyst, 16 cc; T, 572° C.; GHSV, 844 $hr^{-1}$.
[2]AHM = ammonium heptamolybdate; BD = butadiene

EXAMPLE 10 (a–e)

Butane Oxidation

The catalysts (E9 a–e) of Example 9 are employed in the oxidation of butane as described in Example 2 with the results shown in Table IV. It is seen that a potassium-promoted molybdate catalyst supported on an alumina, magnesia spinel composite catalyzes the oxidation of butane to butenes and butadiene in high selectivity. It is further observed that the selectivities to $C_4$ olefins decrease as the concentration of molybdate drops below about 11 weight percent.

EXAMPLE 11

Catalyst Preparation

Alumina spheres (4.09 g; UOP-SAB16) having, a nominal diameter of 1700 μm are impregnated three times to incipient wetness with 10 cc each of a solution containing 1.15 g of MgO as the nitrate hexahydrate. Between each application of the solution the impregnated alumina is calcined at 600° C. for 2 hours thereby yielding a composite support having a $MgO/Al_2O_3$ weight ratio of 0.75. A solution (9.2 ml) containing ammonium heptamolybdate (11.8 g), $K_2CO_3$ (0.228 g) and $NH_4VO_3$ (0.60 g) per 100 ml of solution is added to a sample (6.42 g) of the support, after which the support is calcined to yield a catalyst (E-11) containing 12.03 weight percent $MoO_3$, 0.58 percent $V_2O_5$ and 0.16 percent $K_2O$ and having a surface area of 34 $m^2/g$.

EXAMPLE 12

Butane Oxidation

The catalyst (5.65 g) of Example 11 (E-11) is loaded into a fixed bed reactor as described in Example 2. The reactor is pulsed at 600° C. and a GHSV of 1200 $hr^{-1}$ with a mixture of helium and 20 volume percent butane for a 5-second pulse duration followed by 60-second pulses sequentially of helium, air and helium. The cycle is repeated with the following results: Butane Conversion, 45.2 percent; Selectivities: Butadiene, 58.3 percent; Butenes, 20.6 percent; Sum Butenes, 78.9 percent; Deep Oxidation Products ($CO_2$ and CO), 6.4 percent; Cracking Products, 8.0 percent; and Unknowns, 6.8 percent. The productivity is 0.34 g $C_4$/g cat-hr and 0.25 butadiene/g cat-hr. It is seen that the productivity of $C_4$ carbons and butadiene is greater than the value generally considered to be necessary for a commercial process (0.2 g/g cat-hr).

EXAMPLE 13

Catalyst Preparation

Alumina spheres (713.3 g; UOP-MS-R-27) having particles in the range from about 500 μm to about 1000 μm in diameter are used in preparing an alumina magnesia spinel composite support following the method described in Example 9. A composite support is obtained having a $MgO/Al_2O_3$ weight ratio of 0.38 and a surface area of 106 $m^2/g$. A sample (686 g) of the composite is impregnated with 728 of a solution containing ammonium heptamolybdate (22.5 wt. %) and potassium carbonate (0.66 wt. %). The impregnated composite is calcined at 600° C. for 4 hours to yield a catalyst composition (E-13) containing 18.4 weight percent $MoO_3$ and 0.45 weight percent $K_2O$.

EXAMPLE 14

Butane Oxidation

The catalyst prepared in Example 13 is employed in the oxidation of butane in a laboratory scale riser reactor. A fluidized bed catalyst feed tank (3500 ml capacity) is connected at its bottom to a long tube called the "catalyst standpipe." The standpipe is connected via a "J" valve to a riser, tube about 2 m in length and 6 mm in diameter, which is attached to the first of a series of three cyclone separators connected in sequence. The catalyst recovered in the cyclones is recycled to the top of the catalyst feed tank. A gaseous feedstream comprising 10 volume percent nitrogen, 6.9 volume percent butane and the balance helium is preheated in a preheat tube only 4 mm in diameter, which minimizes the residence time and therefore the thermal cracking of butane. The preheat tube is connected into the system at the juncture of the standpipe and the "J" valve, and the gaseous feedstream is fed at 500 cc/min. The catalyst is heated to a temperature of 650° C. in the feed tank and subsequently fed into the riser tube at a rate of 200 cc/min. The riser tube obtains a temperature of about 580° C. The gas residence time is 1.6 seconds. The catalyst is entrained in the gaseous feedstream with the following results: Butane Conversion, 28.3 percent; Selectivities: Butadiene, 61.9 percent; Butenes, 22.1 percent; Deep Oxidation Products ($CO_2$ and CO), 5.1 percent; $C_{2-3}$ Cracking Products, 7.7 percent; Methane, 1.0 percent; and Unknowns, 2.1 percent. The productivity is about 0.43 g $C_4$/g cat-hr and 0.32 g butadiene/g cat-hr. It is seen that the productivity of $C_4$ carbons and butadiene is greater than the value generally considered to be necessary for a commercial process (0.2 g/g cat-hr).

EXAMPLE 15

Butane Oxidation

The catalyst of Example 13 is employed in the riser reactor described in Example 14 with a gaseous feedstream comprising 67 volume percent butane and the balance nitrogen and helium. The gas feed rate is 1000 cc/min resulting in a gas residence time of about 0.82 sec. The catalyst is fed at a rate of about 455 cc/min with a resulting catalyst residence time of about 3.1 sec. The average temperature in the riser is measured as 584° C. The results are as follows: Butane conversion, 17.1 percent; Selectivities to butadiene, 39.1 percent; butenes, 2.4 percent; deep oxidation products (CO and $CO_2$), 2.5 percent; cracking products, including $C_2-C_3$'s, 10.6 percent and methane, 1.6 percent; isobutane, C.5 percent, and unknowns, 1.8 percent. The productivity of combined butadiene and butene products is 0.94 g $C_4$/g cat-hr, while the productivity of butadiene is 0.49 g butadiene/g cat-hr. It is seen that the productivity of $C_4$ carbons and butadiene is greater than the value generally considered to be necessary for a commercial process (0.2 g/g cat-hr).

What is claimed is:

1. A solid heterogeneous catalyst composition capable of providing a reactive form of oxygen comprising (a) a support component of magnesia and at least one aluminum oxide selected from the group consisting of alumina ($Al_2O_3$) and magnesium aluminate ($MgAl_2O_4$), the support having a $MgO/Al_2O_3$ weight ratio in the range from about 0.3 to about 4.0 and a surface area of at least about 25 $m^2/g$; and (b) a catalyst component consisting essentially of an oxide of magnesium, an oxide of molybdenum, and a promoting amount of a Group IA alkali metal promoter.

2. The catalyst of claim 1 wherein the molybdenum oxide concentration ranges from about 3 weight percent $MoO_3$ to about 50 weight percent $MoO_3$ based on the total weight of the aluminum, magnesium and molybdenum oxides.

3. The catalyst of claim 2 wherein the molybdenum oxide concentration ranges from about 10 weight percent $MoO_3$ to about 30 weight percent $MoO_3$ based on the total weight of the aluminum, magnesium and molybdenum oxides.

4. The catalyst of claim 1 wherein the $MgO/Al_2O_3$ weight ratio ranges from about 0.3 to about 2.0.

5. The catalyst of claim 1 wherein the concentration of the alkali metal promoter ranges from about 0.05 weight percent to about 5 weight percent calculated as alkali metal hydroxide and based on the total weight of the aluminum, magnesium and molybdenum oxides.

6. The catalyst of claim 1 wherein the alkali metal promoter concentration ranges from about 0.1 weight percent to about 2 weight percent.

7. The catalyst of claim 1 wherein the alkali metal promoter concentration ranges from about 0.3 weight percent to about 1.5 weight percent.

8. The catalyst of claim 1 wherein the alkali metal promoter is an alkali metal oxide, hydroxide, carbonate, acetate, or oxalate.

9. The catalyst of claim 8 wherein the alkali metal promoter is an oxide or hydroxide of potassium or cesium.

10. The catalyst of claim 9 wherein the alkali metal promoter is an oxide or hydroxide of potassium.

11. The catalyst of claim 1 having an attrition number less than about 5 weight percent hr$^{-1}$.

12. The catalyst of claim 11 having an attrition number less than about 1 weight percent hr$^{-1}$.

13. The catalyst of claim 1 having a crush strength of at least about 5 lb.

14. The catalyst of claim 13 having a crush strength of at least about 15 lb.

15. The catalyst of claim 1 having a particle size in the range from about 500 μm to about 1200 μm.

16. A solid heterogeneous catalyst composition capable of providing a reactive form of oxygen comprising (a) a support component of magnesia and at least one aluminum oxide selected from the group consisting of alumina ($Al_2O_3$) and magnesium aluminate ($MgAl_2O_4$), the support having a $MgO/Al_2O_3$ weight ratio in the range from about 0.3 to about 4.0 and a surface area of at least about 25 m$^2$/g; and (b) a catalyst component consisting essentially of an oxide of magnesium, an oxide of molybdenum, an oxide of vanadium and a promoting amount of a Group IA alkali metal promoter.

17. The composition of claim 1 wherein the support component has a surface area in the range from about 50 m$^2$/g to about 250 m$^2$/g.

18. The composition of claim 1 having a particle size in the range from about 200 μm to about 1700 μm.

19. The composition of claim 1 wherein the aluminum oxide is a pre-formed magnesium aluminate spinel.

20. The composition of claim 1 wherein the aluminum oxide is in the form of pre-formed alumina spheres having a particle size in the range from about 500 μm to about 1000 μm.

21. The catalyst of claim 1 prepared by a process comprising (a) forming a gel from a mixture of colloidal alumina and magnesia, the $MgO/Al_2O_3$ weight ratio being in the range between 0.3 and 4.0, (b) drying the gel to form a powder, (c) calcining the powder to form a support having a surface area of at least about 25 m$^2$/g, (d) impregnating the support with a solution of a molybdenum salt and a Group IA alkali metal promoter, and (e) calcining the impregnated support to obtain a supported catalytic component comprising an oxide of magnesium, an oxide of molybdenum, and an oxide of an alkali metal.

* * * * *